United States Patent [19]
Ehrmann et al.

[11] Patent Number: 5,457,224
[45] Date of Patent: Oct. 10, 1995

[54] RESOLUTION OF RACEMIC VERAPAMIL

[75] Inventors: Oskar Ehrmann, Mannheim-Neuhermsheim; Herbert Nagel, Schifferstadt, both of Germany

[73] Assignee: Knoll Aktiengesellschaft, Ludwigshafen, Germany

[21] Appl. No.: 244,681

[22] PCT Filed: Jan. 9, 1993

[86] PCT No.: PCT/EP93/00196

§ 371 Date: Jun. 7, 1994

§ 102(e) Date: Jun. 7, 1994

[87] PCT Pub. No.: WO93/16035

PCT Pub. Date: Aug. 19, 1993

[30] Foreign Application Priority Data

Feb. 7, 1992 [DE] Germany ............ 43 03 547.3

[51] Int. Cl.⁶ .................... C07C 253/30; C07C 253/34
[52] U.S. Cl. ............................. 558/354; 558/390
[58] Field of Search ...................... 558/354, 390

[56] References Cited

U.S. PATENT DOCUMENTS 4,305,887  12/1981  Herrling ................... 260/465

FOREIGN PATENT DOCUMENTS

| 0029175 | 5/1981 | European Pat. Off. . |
| 3723684 | 1/1989 | Germany . |
| 999612 | 7/1965 | United Kingdom . |
| 1367677 | 9/1974 | United Kingdom . |

OTHER PUBLICATIONS

"The American Heritage Dictionary", 2nd College Edition, p. 873, (1982).
"Academic Press Dictionary of Science and Technology," Edited by Christopher Morris, p. 1523, (1985), Academic Press, N.Y.
Helvetica Chimica Acta. vol. 58, Fasc 7 (1975); Ramuy, pp. 2050–2060.

*Primary Examiner*—Joseph Paul Brust
*Attorney, Agent, or Firm*—Keil & Weinkauf

[57] ABSTRACT

A process for the resolution of racemic verapamil which comprises reacting the free base of the compound with optically active dibenzoyltartaric acid or ditoluoyltartaric acid in the molar ratio from 1:1 to 1:2 in a methanol/water mixture in the ratio from 1:1 to 3:1 or acetone/water mixture in the ratio from 0.5:1 to 2:1, separating the mixture of diastereomers obtained in this way by crystallization, and then converting the diastereomers into the free bases and these into their salts, if required, with physiologically tolerated acids.

5 Claims, No Drawings

RESOLUTION OF RACEMIC VERAPAMIL

Verapamil [1,7-bis(3,4-dimethoxyphenyl)-3-methyl-aza-7-cyano-8-methylnonane] has been disclosed in DE-C 1 154 810. It was for a long time not possible to resolve this racemic compound into the optical antipodes (Helv. Chim. Acta 58 (1975) 2050). It was therefore necessary to synthesize it from optically active precursors (DE-C 20 59 985, DE-C 20 59 923).

EP-C 29 175 describes the resolution of racemic gallopamil with the aid of the O,O'-dibenzoyl derivative of unnatural (+)-D-tartaric acid. However, the resolution of racemic verapamil is not described in this patent.

By contrast, DE-A 3 723 684 describes a process for the resolution of racemic verapamil with the aid of R- or S-2,2'-(1,1'-binaphthyl)phosphoric acid. However, this substance is extremely costly to prepare so that economic preparation of the antipodes of verapamil continues to be impossible.

It was necessary to assume from this prior art that resolution of racemic verapamil is very difficult and costly.

We have now found a very favorable process which can be used to resolve verapamil into its antipodes.

The present invention relates to a process for the resolution of racemic verapamil, which comprises reacting the free base of the compound with optically active dibenzoyltartaric acid or ditoluoyltartaric acid in the molar ratio from 1:1 to 1:2 in a methanol/water mixture in the ratio from 1:1 to 3:1 or acetone/water mixture in the ratio from 0.5:1 to 2:1, separating the mixture of diastereomers obtained in this way by crystallization, and converting the diastereomers obtained in this way into the free bases and subsequently into their salts if required.

Verapamil and the optically active acid are reacted together in the molar ratio from 1:1 to 1:2, preferably 1:1.5. On cooling the solution in methanol/water or acetone/water, the salt of one antipode crystallizes out while the other antipode remains in the mother liquor. When the acid used is (−)-O,O'-dibenzoyl-L-tartaric acid, the dibenzoyl-L-tartrate of (S)-verapamil crystallizes out first, and if it is (+)-O,O'-dibenzoyl-D-tartaric acid, the dibenzoyl-D-tartrate of (R)-verapamil crystallizes out first.

After removal of the precipitated diastereomeric salt, the solvent is removed by distillation, and the base is liberated from the residue and converted with the other enantiomeric form of O,O'-dibenzoyltartaric acid into the hydrogen tartrate. The procedure for the ditoluyltartaric acid salts corresponds. The dibenzoyl and ditoluoyl derivatives of natural L-tartaric acid are advantageously employed for the racemate resolution.

The resolution of racemic verapamil is particularly advantageous and low-cost on addition of an inorganic mineral acid. This makes it possible to save up to 1.5 mol of the tartaric acid per mol of verapamil. It is most favorable to carry out the resolution with optically active dibenzoyl-or ditoluoyltartaric acid in the presence of mineral acid in the molar ratio 1: 0.75:0.5 (verapamil : tartaric acid : mineral acid). The crystallizing diastereomeric salt of one enantiomer has the same optical purity. The other enantiomer remains in solution and can be isolated therefrom in a conventional manner, for example by concentration of the solution. Particularly suitable mineral acids are phosphoric acid and sulfuric acid, and hydrochloric acid is preferably used.

(R)- or (S)-verapamil is liberated from the diastereomeric salts in a conventional way using a base in aqueous medium and is isolated by extraction. The bases obtained in this way can be converted into their salts with physiologically tolerated acids by conventional processes.

EXAMPLE 1 a) 250 g (0.55 mol) of racemic verapamil and 310 g (0.82 mol) of (−)-O,O'-dibenzoyl-L-tartaric acid hydrate were dissolved by heating in 1.3 l of methanol/water=2:1. The crystals which separated out overnight were filtered off with suction and dried. The crystals have a melting point of 103°–107° C. and a rotation $[\alpha]^{20}_D=-53.3°$ (ethanol, c=15 mg/ml). The crystals obtained after three recrystallizations from methanol/water=2:1 had a melting point of 113°–115° C. and the rotation $[\alpha]^{20}_D=-66.2°$ (ethanol, c=15 mg/ml). This figure did not change on recrystallization once again. The base liberated from the salt with sodium hydroxide solution was directly converted into the hydrochloride. Recrystallization once from diisopropyl ether/isopropanol= 3:2 resulted in 83.7 g (62%) of (S)-verapamil hydrochloride with melting point 131–133° C. and rotation $[\alpha]^{20}_D=-9.2°$ (ethanol, c=50 mg/ml). The figure did not change on crystallization once more.

b) The mother liquor resulting from the precipitation in a) was concentrated under reduced pressure, the residue was taken up in water, and the base was liberated therefrom by adding 1 M sodium hydroxide solution. Extraction with toluene, drying over sodium sulfate and removal of the solvent by distillation resulted in isolation of an oil.

This oil and 155 g (0.41 mol) of (+)-O,O'-dibenzoyl-D-tartaric acid hydrate were dissolved by heating in 650 ml of methanol/water=2:1. The crystals which separated out overnight were filtered off with suction and dried. The crystals have a melting point of 105°–109° C. and a rotation of $[\alpha]^{20}_D=+61.5°$ (ethanol, c=15 mg/ml). The salt was recrystallized twice from methanol/water 2:1. Crystals of melting point 113°–115° C. and with a rotation of $[\alpha]^{20}_D=+66.8°$ (ethanol, c=15 mg/ml) were obtained. The figure did not change on crystallization once more.

The base liberated from the salt was converted into the hydrochloride. A single recrystallization from diisopropyl ether/isopropanol 3:2 resulted in 78.3 g (58%) of (R)-verapamil hydrochloride of melting point 129°–131° C. and rotation $[\alpha]^{20}_D=+9.2°$ (ethanol, c=50 mg/ml). This figure did not change on further recrystallization.

EXAMPLE 2

Example 1 was repeated but (+)-O,O'-dibenzoyl-D-tartaric acid was used in a) and (−)-O,O'-dibenzoyl-L-tartaric acid was used in b). The result was the same as in Example 1 but the antipodes were obtained in reverse sequence.

EXAMPLE 3

The procedure was as in Examples 1 and 2 but the optically active forms of O,O'-di-4-toluoyltartaric acid were used in place of the optically active forms of 0,0'-dibenzoyltartaric acid, and the (S) and (R) forms of verapamil hydrochloride were likewise obtained.

EXAMPLE 4

The procedure was as in Examples 1a, 1b, 2 and 3, but methanol/water=2:1 was replaced by acetone/water=1:1 (twice the volume), and the (R) and (S) forms of verapamil hydrochloride were likewise obtained.

EXAMPLE 5

250 g ( 0.55 mol ) of racemic verapamil, 155 g (0.41 mol) of (−)-O,O'-dibenzoyl-L-tartaric acid hydrate and 10 g ( 0.275 mol ) of hydrogen chloride were dissolved by heating in 2500 ml of methanol/water =1:1.

The crystals which separated out overnight were filtered off with suction and recrystallized as described in Example 1. The result was the same as in Example 1.

The process was repeated with (+)-O,O'-dibenzoyl-D-tartaric acid. The result was the same as in Example 2.

The (S) and (R) forms of verapamil hydrochloride were likewise obtained with the optically active forms of O,O'-ditoluoyltartaric acids.

What is claimed is:

1. A process for the resolution of racemic verapamil, which comprises reacting the free base of the compound with optically active dibenzoyltartaric acid or Optically active ditoluoyltartaric acid in the molar ratio of from 1:1 to 1:2 in a methanol/water mixture in the ratio from 1:1 to 3:1 or acetone/water mixture in the ratio from 0.5:1 to 2:1, and in the presence of an at least 0.5 molar amount per note of verapan free base of an inorganic mineral acid, and separating the mixture of diastereomers obtained in this way by crystallization.

2. A process as defined in claim 1, wherein a quantity of the optically active dibenzoyltartaric acid or optically active ditoluoyltartaric acid up to 50% is replaced by an inorganic mineral acid.

3. A process as defined in claim 1, wherein the verapamil is reacted with optically active dibenzoyltartaric acid or ditoluoyltartaric acid in the molar ratio 1:0.75 in the presence of 0.5 mol of hydrochloric acid.

4. The process of claim 2, wherein the mineral acid is hydrochloric acid.

5. The process of claim 1, wherein the diastereomers separated by crystallization are converted into free bases and then into salts.

* * * * *

UNITED STATES PATENT AND TRADEMARK OFFICE
CERTIFICATE OF CORRECTION

PATENT NO.: 5,457,224

DATED: October 10, 1995

INVENTOR(S): EHRMANN et al.

It is certified that error appears in the above-identified patent and that said Letters Patent is hereby corrected as shown below:

On the title page, item [22], replace "Jan. 9, 1993" with --Jan. 28, 1993--.

Column 4, claim 1, line 2, "per note of" should read --(per mole of--;

line 3, "verapan" should read --verapamil--; and line 3, after "base" insert --)--.

Signed and Sealed this

Nineteenth Day of December, 1995

*Attest:*

BRUCE LEHMAN

*Attesting Officer*      *Commissioner of Patents and Trademarks*